United States Patent
Torres et al.

(10) Patent No.: US 8,921,624 B2
(45) Date of Patent: Dec. 30, 2014

(54) PROCESS FOR PRODUCING N-PROPYL BROMIDE OR OTHER ALIPHATIC BROMIDES

(75) Inventors: James E. Torres, Baton Rouge, LA (US); Alvin E. Harkins, Jr., Baton Rouge, LA (US); Thanikavelu Manimaran, Baton Rouge, LA (US); B. Gary McKinnie, Magnolia, AR (US)

(73) Assignee: Albemarle Corporation, Richmond, VA (US)

( * ) Notice: Subject to any disclaimer, the term of this patent is extended or adjusted under 35 U.S.C. 154(b) by 1238 days.

(21) Appl. No.: 12/296,629

(22) PCT Filed: Apr. 11, 2007

(86) PCT No.: PCT/US2007/066409
§ 371 (c)(1),
(2), (4) Date: Oct. 9, 2008

(87) PCT Pub. No.: WO2007/121228
PCT Pub. Date: Oct. 25, 2007

(65) Prior Publication Data
US 2009/0054709 A1    Feb. 26, 2009

Related U.S. Application Data

(60) Provisional application No. 60/791,850, filed on Apr. 13, 2006.

(51) Int. Cl.
 C07C 21/00        (2006.01)
 C07C 17/08        (2006.01)
(52) U.S. Cl.
 CPC .................................. *C07C 17/08* (2013.01)
 USPC ........................................................ 570/246

(58) Field of Classification Search
 CPC combination set(s) only.
 See application file for complete search history.

(56) References Cited

U.S. PATENT DOCUMENTS

| | | | |
|---|---|---|---|
| 3,321,536 A | 5/1967 | Plesmid | |
| 5,527,975 A | 6/1996 | Cosserat et al. | |

FOREIGN PATENT DOCUMENTS

| | | |
|---|---|---|
| GB | 841745 | 7/1960 |
| GB | 927114 | 5/1963 |
| JP | S36-12267 B | 8/1961 |
| JP | S41-19524 B | 11/1966 |
| WO | 2006113307 A1 | 10/2006 |

OTHER PUBLICATIONS

Derwent abstract Guseinov, M. et al, SU-182126, 1966, 1-2.*
Chemical Abstracts Service, abstract No. 2004:627051, abstract of SK 282980, Macho, Vendelin et al., "Selective hydrobromination of olefinically unsaturated compounds".

* cited by examiner

*Primary Examiner* — Clinton Brooks
(74) *Attorney, Agent, or Firm* — Marcy M. Hoefling

(57) ABSTRACT

A process for the production of an aliphatic bromide in which the bromine atom is attached to a terminal carbon atom, which process comprises continuously feeding olefin having a terminal double bond, gaseous hydrogen bromide, and a molecular oxygen-containing gas into a liquid phase reaction medium comprised of aliphatic bromide to cause anti-Markovnikov addition of HBr to terminal olefin, the feeds being proportioned and maintained to provide a molar excess of hydrogen bromide relative to terminal olefin in the range of about 1 to about 5 percent, and a molar ratio of molecular oxygen to terminal olefin of less than 0.005. The process is especially suited for production of n-propyl bromide.

23 Claims, 4 Drawing Sheets

US 8,921,624 B2

PROCESS FOR PRODUCING N-PROPYL BROMIDE OR OTHER ALIPHATIC BROMIDES

REFERENCE TO RELATED APPLICATIONS

This application is the National Stage of International Patent Application PCT/US2007/066409, filed on Apr. 11, 2007, which application claims priority from U.S. Application No. 60/791,850, filed Apr. 13, 2006, the disclosures of which are incorporated herein by reference.

TECHNICAL FIELD

This invention relates to an improved process for preparing aliphatic bromides, especially n-propyl bromide alone or along with isopropyl bromide.

BACKGROUND

A process for preparing aliphatic bromides in which the bromine atom is attached to a terminal carbon atom is described in Brit. 841,745, published Jul. 20, 1960, all disclosure of which is incorporated herein by reference. The process comprises passing hydrogen bromide and molecular oxygen into a solution of a terminal olefin ($CH_2=CR_1R_2$, where $R_1$ is hydrogen, alkyl, or haloalkyl, and $R_2$ is alkyl, or haloalkyl) in the aliphatic bromide product. The molar proportion of hydrogen bromide in solution in not substantially in excess of that of the olefin used, and preferably is a molar proportion of olefin to hydrogen bromide of at least 1:1. The volume of molecular oxygen passed through the reaction mixture identified is between 0.01-1 mole of oxygen per mole of hydrogen bromide fed. Air is identified as a suitable source of oxygen.

The production of n-propyl bromide by free-radical (anti-Markovnikov) addition of HBr to propylene using air typically results in a selectivity of about 97% for n-propyl bromide (NPB), with >99.5% reaction completion. Typically some isopropyl bromide (IPB) is co-produced and this is of use as an article of commerce. However, in such processing, trace levels of elemental bromine are formed the reaction. Studies in our laboratories have shown that formation of trace amounts of bromine and peroxy radicals leads to the formation of small amounts of various other by-products such as 1,2-dibromopropane, acetone, bromoacetone, propionaldehyde, 1,3-dibromoacetone, 1-propanol, and 2-propanol. The formation of acetone and bromoacetone, typically at levels of about 200 ppm, is especially undesirable as bromoacetone even at such low concentrations is a powerful lachrymator. Also when it is desired to recover isopropyl bromide as a co-product, acetone is troublesome as it readily dissolves in isopropyl bromide thus necessitating another separation step.

In the case of $C_4$ and higher aliphatic bromides in which the bromine atom is attached to a terminal carbon atom, formation of analogous undesirable impurities during their production by hydrobromination is also deemed disadvantageous.

It would be of considerable advantage if a way could be found of minimizing or suppressing the formation of such undesirable by-products, thereby enabling recovery of high quality product such as NPB, even if by-product HBr feedstock containing some HCl is used in the process. It would also be advantageous if the way of accomplishing these goals would likely be applicable to use of the same technology in the production of other aliphatic bromides. This invention is believed to provide an efficient and effective way of achieving these goals.

BRIEF SUMMARY OF THE INVENTION

It has been discovered that use of feeds of molecular oxygen in amounts that are much below, and preferably that are at least about an order of magnitude lower than, the levels taught in Brit. 841,745, enable the hydrobromination of propylene to proceed efficiently and with minimization or suppression of undesirable by-product formation, thereby enabling recovery of highly pure NPB, and also IPB as a separate co-product if desired. From the results obtained on hydrobromination of propylene using air (of which molecular oxygen is the active component) it is reasonable to expect that pursuant to this invention similar advantages in by-product minimization or suppression can be achieved with other terminal olefins and haloolefins such as referred to in Brit. 841,745.

These and other features and embodiments of this invention will be still further apparent from the ensuing description and appended claims.

BRIEF DESCRIPTION OF THE DRAWING

In the Figures of the Drawings, in which like numerals are used to depict like parts among the several Drawings.

FURTHER DETAILED DESCRIPTION OF THE INVENTION

Figure 1:
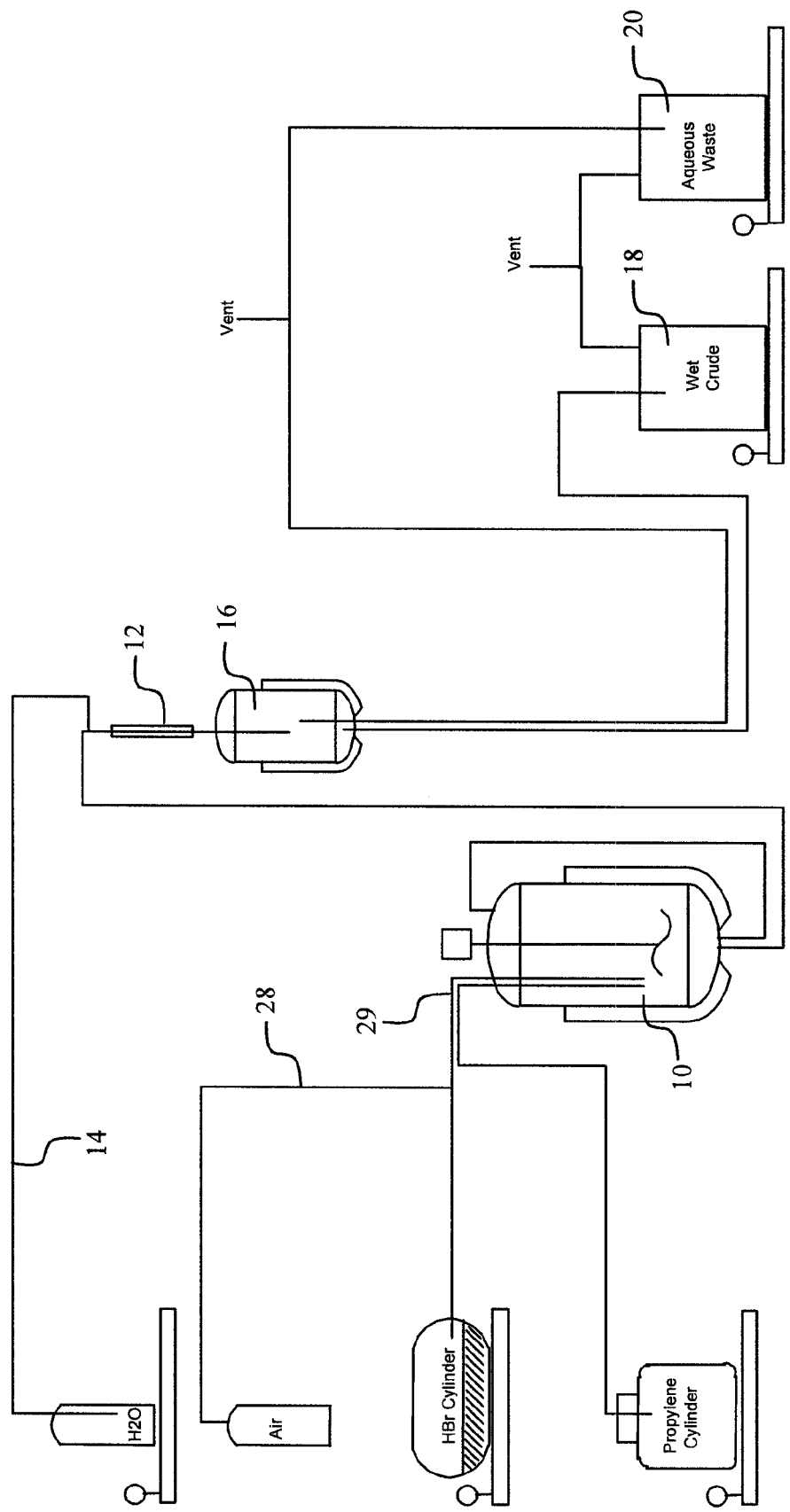
FIG. 1 is a schematic flow diagram of a hydrobromination reaction system for use in the production of n-propyl bromide.

Provided by this invention is a distinct improvement in the process for production of aliphatic bromides described in Brit. 841,745. Thus this invention provides a process for the production of an aliphatic bromide in which the bromine atom is attached to a terminal carbon atom, which process comprises continuously feeding hydrobrominatable aliphatic olefin having a terminal double bond (for convenience, often referred more simply as terminal olefin), gaseous hydrogen bromide, and a molecular oxygen-containing gas into a liquid phase reaction medium to cause anti-Markovnikov addition of HBr to the terminal double bond of the terminal olefin to form 1-bromoalkane, usually with a small amount of addition of HBr to the terminal double bond to form 2-bromoalkane. For best results, the terminal olefin used should be of high purity. For example, the terminal olefin feed should be free or at least substantially free of hydrobrominatable olefins or other unsaturates other than the terminal olefin to be hydrobrominated in the reaction. This will enable formation of the desired 1-bromoalkane product in high yields and with high selectivity and avoid or minimize formation of a mixture of various hydrobrominated products requiring subsequent handling and purification in order to obtain the desired 1-bromoalkane product (and 2-bromoalkane co-product when desired). While saturated hydrocarbon can be present in admixture with the terminal olefin feed, this is not preferred as it requires handling of inerts in the process, lessens plant output of desired product, and can necessitate additional purification in order to recover the desired 1-bromoalkane product (and 2-bromoalkane co-product when desired). Thus the higher the purity of the terminal olefin feed, the better.

The hydrogen bromide feed can be pure or it can be substantially pure, i.e., under suitable process conditions this invention is capable of utilizing hydrogen bromide containing up to about 4-5 mole percent of hydrogen chloride. In the case hyrobromination of propylene, operating conditions have been discovered which eliminate or at least greatly suppress formation of acetone and bromoacetone impurities during hydrobromination.

Various forms of molecular oxygen-containing gas can be used in the process. Use of dry air, especially dry air free of pollutants and particulates, is preferred because of availability and low cost. However, pure oxygen, air enriched with oxygen, or a mixture of an inert gas such as nitrogen, argon, or neon with oxygen, are among suitable forms of molecular oxygen-containing gases that can be used in the process. Preferably a mixture of air and nitrogen containing 9 to 11 mole %, and typically about 10 mole %, of molecular oxygen is used.

The liquid phase reaction medium is preferably a portion of the hydrobromination product being produced, and thus at start up a suitable quantity of such product should be introduced and maintained in the reaction zone until steady state hydrobromination has been achieved. In the case of propyl bromide production it is desirable to conduct start up using propyl bromide saturated with hydrogen bromide as the initial reaction medium. Thereupon the introduction of such product can be discontinued as the product being produced in the hydrobromination serves as in situ formed liquid phase for the hydrobromination reaction.

Interruptions of the continuous feeds that do not materially interfere with the overall steady state operation of the plant can be tolerated, and are contemplated by and are within the scope of the term "continuous", and thus are within the scope of this invention. Moreover the term "continuous" does not imply that the feeds must start at the same time or cease at the same time.

The hydrobromination reaction is typically performed at a suitable temperature, which can be as low as, say, about −40° C. and as high as about 50° C. When preparing n-propyl bromide using hydrogen bromide containing up to about 4-5 mole percent of hydrogen chloride impurity, preferably the hydrobromination reaction is performed in a temperature range of about −40 to about 5° C., more preferably in a temperature range of about −20 to about 5° C., and still more preferably in a temperature range of about 0 to about 5° C. It is also desirable to perform the reaction in a "buttoned-up" hydrobromination reaction zone (i.e., there is no separate vent of gas from the reactor). These conditions, together with the very low molecular oxygen levels fed to the reaction zone pursuant to this invention, eliminate or at least minimize the formation of undesirable amounts of acetone and bromoacetone in the hydrobromination reaction zone. On the other hand, when preparing n-propyl bromide pursuant to this invention using hydrogen bromide free or substantially free of hydrogen chloride impurity, and using the very low molecular oxygen levels fed to the reaction zone whereby undesirable amounts of acetone and bromoacetone are not formed in the hydrobromination reaction zone, operation in a temperature range of about −40° C. to about 50° C. can be used.

The hydrobromination reaction can be conducted at atmospheric pressures, subatmospheric pressures, or superatmospheric pressures. Typically, however, the hydrobromination reaction zone or reactor is operated at autogenous pressure which may extend from moderately reduced pressures to mild superatmospheric pressures. Pressure can be reduced by operating at very low temperatures, by reducing the amount of inert gases present in the feed when using air, or when hydrogen chloride is present, by minimizing the amount of HCl in the feed. Pressure can be increased by operating at higher temperatures, by increasing the amount of inert gases present in the feed when using air, or when hydrogen chloride is present, by increasing the amount of HCl in the feed. Operations have been successfully conducted at a pressure in the range of about 8 to about 10 pounds per square inch above atmospheric pressure. Excess hydrogen bromide relative to terminal olefin is fed into the reaction zone, which excess preferably is in the range of about 1 to about 5 mole percent, and more preferably in the range of about 1 to about 3 mole percent excess. Pursuant to this invention, the molar ratio of molecular oxygen to terminal olefin is kept below 0.005:1, typically in the range of about 0.00005:1 to about 0.001:1 and preferably in the range of about 0.00005:1 to about 0.0001:1. Operation of the reaction with such modest excess of HBr leads to nearly 100% conversion of propylene, and operation of the reaction with such extremely low levels of molecular oxygen results in minimization or suppression of formation of highly undesirable by-products including acetone and bromoacetone, as well as others referred to above.

Various terminal olefins can be used. The chief requirement is that the terminal double bond is susceptible to hydrobromination. Terminal olefin containing bromine or chlorine substituents can be used. However, terminal olefins that are hydrobrominatable 1-alkenes having at least three carbon atoms in the molecule are preferred. A few non-limiting example of suitable terminal olefins with and without bromine or chlorine substituents include propylene (a.k.a. propene), 1-butene, isobutylene (a.k.a. 2-methylpropene), 1-pentene, 4-methyl-1-butene, 1-hexene, 4-methyl-1-pentene, 1-heptene, 1-octene, 2-ethyl-1-hexene, 1-decene, 3-chloro-1-butene, and allylbromide. Use of propylene is preferred.

Preferably a feed of air or other molecular oxygen-containing gas is premixed with a feed of gaseous hydrogen bromide so that both substances are in a combined unitary feed. The terminal olefin is typically introduced into the reaction zone as a separate feed, although other modes of feeding are possible. One should be careful to avoid potential explosive limits if terminal olefin and air or other molecular oxygen-containing gas are to be premixed as a combined or unified feed. Thus although a combined premixed feed of terminal olefin and air or other molecular oxygen-containing gas is possible, it is not recommended.

When using HBr that is devoid or contains only trace amounts of HCl, the hydrobromination can be performed at elevated pressure (e.g., 5-25 psig minimum) and at temperatures in the range of about −40° C. to about 50° C., and preferably at moderate temperatures in the range of about 20 to about 45° C. If HCl impurity is present in more than trace amounts in the HBr (e.g., in amounts in the range of about 0.1 to about 5 mole %), it is preferable to operate the hydrobromination at temperatures in the range of about 0 to about 5° C. at autogenous pressures in a closed reaction system, or at temperatures in the range of about −10 to about 50° C. at lower autogenous pressures in a non-sealed reaction zone. The presence of HCl, common at up to 4 mole % in the plant-site by-product HBr, can lead to the formation of normal- and iso-propyl chloride as well as other by-product chloride species.

Presence of metals, such as iron, can suppress free radical reactions and encourage ionic side reactions, resulting, for example, in decreased NPB selectivity & yield. Thus reaction equipment should be selected to minimize if not eliminate exposure of the reactants and reaction mass to metals such as ferrous metals.

The excess HBr from the reaction mass can be absorbed by mixing the reactor effluent stream with water to form dilute hydrobromic acid. Water and n-propyl bromide are only slightly soluble in one another (~1000's of ppm), and thus aqueous washing can decrease the amount of HBr in the organic phase to a few hundred ppm or less.

Drying of the wet organic phase can be accomplished by distillation (reboiled stripping), as this is not a difficult separation as long as a free water phase is not present in the column. The water is more volatile than the organic, and comes out in the distillate. The HBr and acetone are more volatile than the water, and thus the levels of water, acetone, and levels of HBr of about 1 ppm can be achieved in the column reboiler, but levels up to about 10 ppm can be tolerated in the column reboiler.

Separation of isopropyl bromide from normal propyl bromide is a more difficult separation than water removal. This distillation requires a large number of stages and a high reflux ratio. The distillate is made up mostly of isopropyl bromide and the other light components, such as acetone and propyl chloride.

To remove the heavy components from the n-propyl bromide, mainly dibromopropane and propionic acid, a third distillation can be used. This separation is easier than the isopropyl bromide separation. Normal propyl bromide purities of 99.99% are achievable.

Referring now to the Drawings, in a hydrobromination reaction system as depicted FIG. 1, propylene, HBr, and air are fed to reactor 10 where the hydrobromination reaction takes place. In this system, reactor 10 is a glass-lined jacketed reactor equipped with an exterior liquid level indicator. The reaction mass, produced in reactor 10 under reaction conditions described above, travels up a two-phase lift to a static mixer 12, where it is mixed with a water stream from line 14. The static mixer empties into a separator system 16 in which the organic phase product and water are separated from each other. Separator unit 16 is depicted in, and described in greater detail, in connection with FIG. 4 hereinafter. Still referring to FIG. 1, the organic phase is drained to a crude product drum 18 made of perfluoroalkoxyalkane polymer (PFA), and the aqueous phase is drained to a waste drum 20. The vent lines from the drums can be tied to a knockout pot, caustic bath, and carbon drum (not shown). The n-propyl bromide in the organic phase is dried and purified by distillation.

Figure 2:
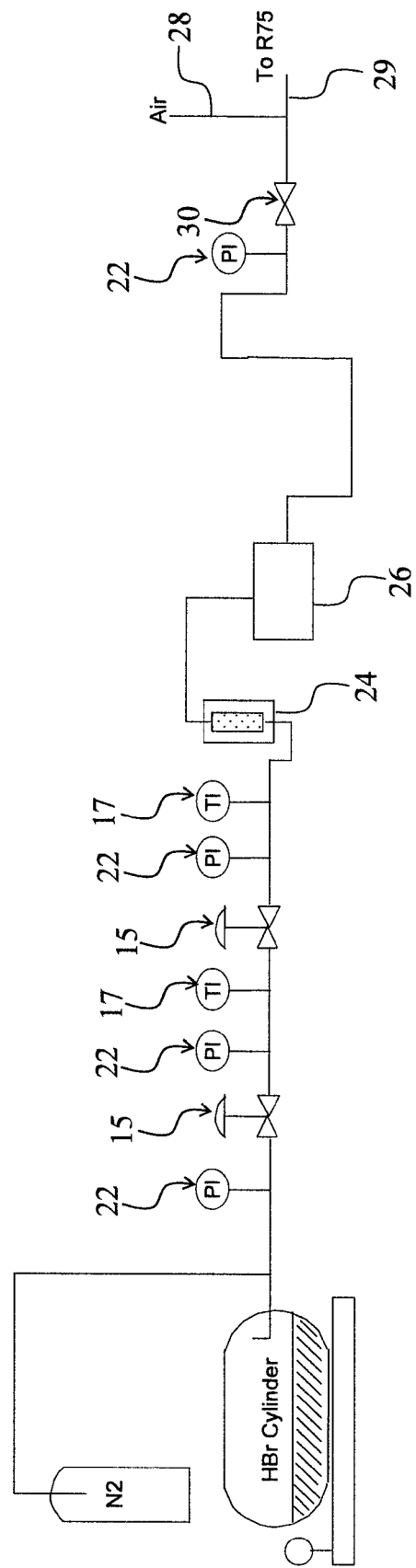
FIG. 2 is a schematic depiction of an HBr feed system that can be used in the reaction system of FIG. 1.

A typical HBr feed system that can be used in a hydrobromination reaction system is schematically depicted in FIG. 2. In this system, nitrogen is used for pressure testing and to purge HBr from the lines prior to performing line breaks. The HBr feed cylinders are placed on a 4'×4' In scale low profile floor scale. The scale has a GSE digital weight indicator, and the indicator displays weight to the nearest pound. The HBr pressure is regulated with two Tescom electrically-heated vaporizing regulators 15,15. Use of two regulators ensures that single regulator failure would not overpressure the hydrobromination reactor 10. Pressure of the feed line is measured upstream, between, and downstream of the regulators using three Monel body Chemseal pressure indicators 22,22,22 with tantalum diaphragms. Temperature of the feed line is measured using two Ametek/US Gauge DT-8300 Series Digital Temperature Indicators 17,17. The HBr is then passed through a Simplex Basket Strainer 24, packed with fiberglass wool to remove iron bromide. The flow rate of HBr is measured using a Micro Motion mass flow sensor 26.

The HBr then becomes mixed with air or other molecular oxygen-containing gas entering at air feed line 28, and the resultant mixed feed proceeds into reactor 10. The HBr flow upstream from the tie to line 28 includes a ¼ turn block valve 30 which is used to help control the flow rate for pressure driven flow. The valve is kept cracked open, increasing the pressure drop of the flow to reactor 10. Increasing the pressure drop decreases the magnitude of the fluctuations in flow rate to reactor 10 that may be caused by oscillations of reactor pressure. Another Monel body Chemseal pressure indicator 22 with a tantalum diaphragm is located upstream from the block valve 30. The material of the lines used in the HBr feed system should be of acid resistant materials such as monel or Teflon polymer.

The propylene feed system is mechanically similar to the HBr system just described with the components being constructed of stainless steel instead of monel. The propylene cylinder is placed on a 4'×4' floor scale having a digital weight indicator displaying weight to the nearest half pound. The propylene pressure is regulated with two Tescom electrically-heated vaporizing regulators. Use of two regulators ensures that single regulator failure would not overpressure reactor 10. Pressure of the feed line is measured upstream, between, and downstream of the regulators using three pressure indicators. Temperature of the feed line is measured using two Ametek/US Gauge DT-8300 Series Digital Temperature Indicators. The flow rate of the propylene is controlled by a Brooks thermal mass flow sensor with integral control valve. This sensor is connected to a local Fieldpac PID controller. The controller reads the feed rate of the HBr from the Micro Motion mass flow sensor, and controls the propylene rate to a desired ratio. The propylene is then passed through a glass rotometer (Cole-Parmer 03219-35) and sent to reactor 10. The material of construction of the propylene feed system should be a corrosion resistant material such as stainless steel.

The sources of air that can be used are ordinary plant air (breathing air) and air from a zero water IA cylinder. In humid areas, the plant air should be dried by passage over molecular sieves and filtered. Typically, cylinder air is merely filtered. The air pressure is regulated and the flow is measured using a glass rotometer. As indicated in FIG. 2, the air line is tied into the HBr line prior to entry to reactor 10.

Figure 3:
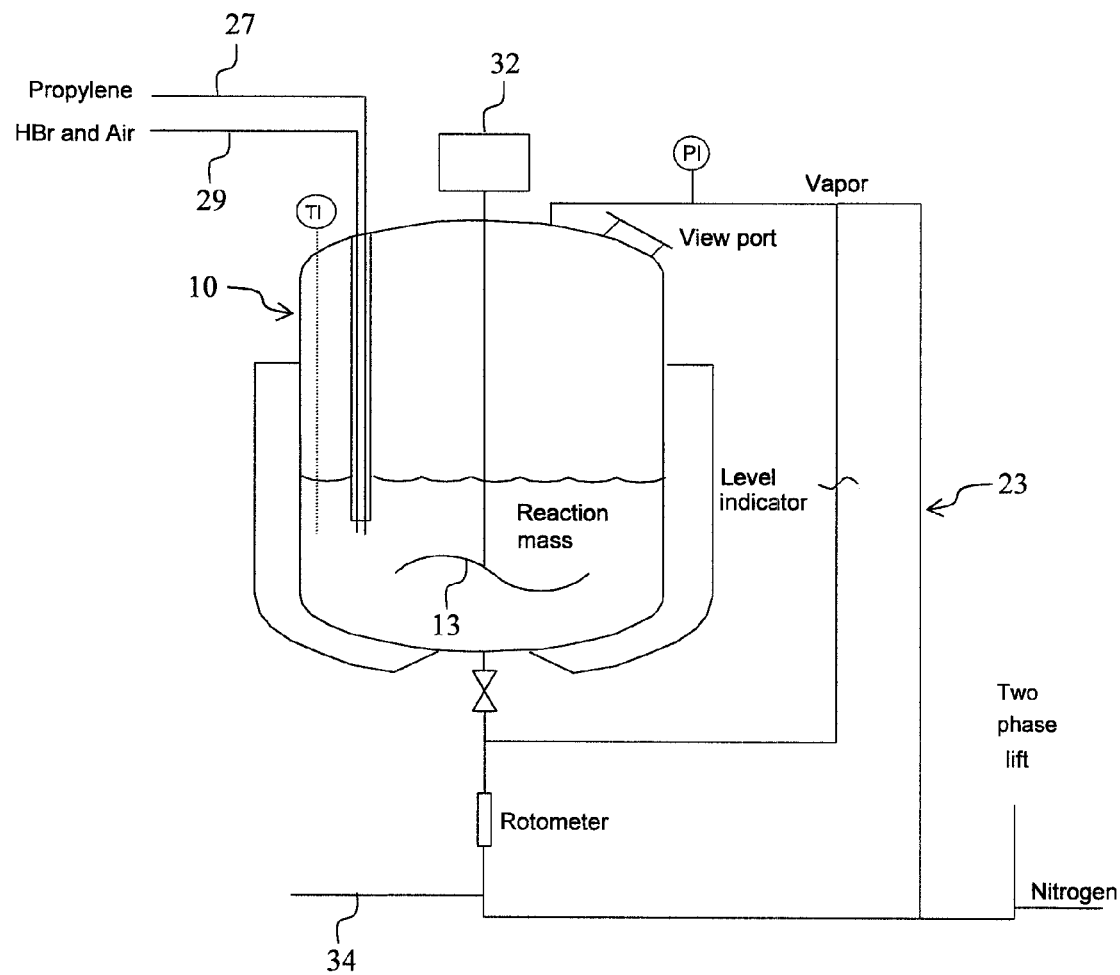
FIG. 3 is a schematic diagram of a hydrobromination reactor that can be used in the reaction system of FIG. 1.

The reaction is carried out in reactor 10, details of which are schematically depicted in FIG. 3. Reactor 10 can be a glass-lined, jacketed vessel with a pressure rating of 150 psi. Reactor 10 is preferably equipped with a 16" Nucerite Retreat Curve Impeller 13, located 4.5" above the bottom of the pot. The propylene feed line 27 and HBr/air feed line 29 to reactor 10 enter the reaction mass subsurface. Such feed lines are made of PFA. During operation of the particular system depicted, the impeller is typically run at 60 rpm, and the seal pressure on the agitator motor 32 is kept 20 psi higher than the reaction pressure. Line 23 serves as a reactor vapor discharge and provides motive vapor for a two phase lift. The temperature of reactor 10 is controlled using a pump around unit (not shown). The pump around unit includes a pump (not shown) which circulates ethylene glycol into, through, and out of the reactor jacket, with cold ethylene glycol entering the jacket and warmed ethylene glycol exiting the jacket. A flow control valve, under the control of a Watlow Series 965 temperature controller adjusted to the desired temperature, controls the flow in the pump around unit. The pressure is controlled using a Teflon polymer backpressure regulator (not shown). The effluent from reactor 10, liquid and vapor, travels to the static mixer 12 (shown in FIG. 1) via the two-phase lift. Prior to entry to the static mixer, water is mixed with the reaction mass. Sample line 34 from reactor 10 runs to a nitrogen purge box (not shown). A 100 psi rupture disk (not shown) is installed on reactor 10 for safety reasons.

Figure 4:
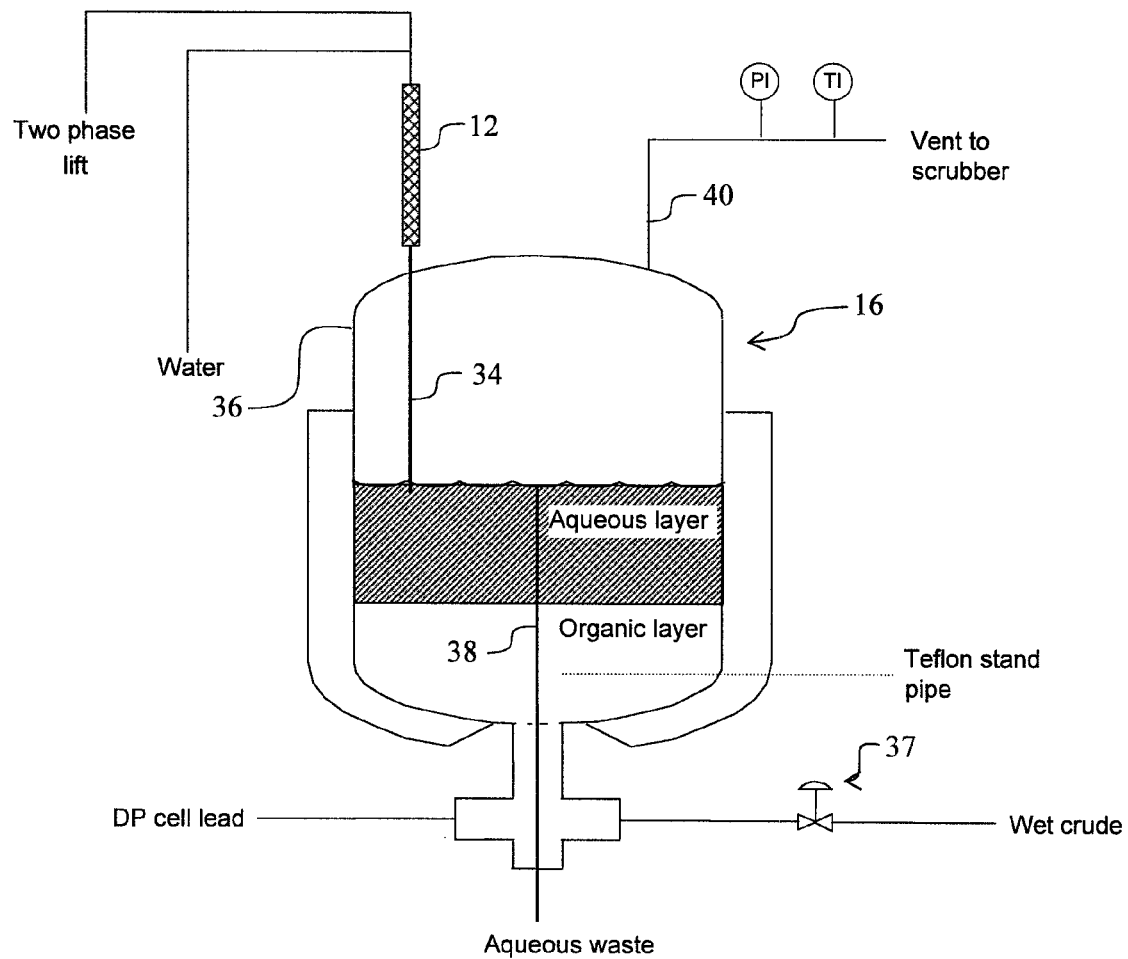
FIG. 4 is a schematic flow diagram of a separator unit that can be used in the reaction system of FIG. 1.

FIG. 4 depicts schematically in more detail a liquid-liquid separator system 16 that can be used in the reaction system of FIG. 1 to separate the water and wet organic crude hydrobromination product mixture. For this purpose, a glass-lined jacketed vessel 36 is used as the separator unit. A Teflon polymer standpipe 38 is used to maintain a maximum liquid level in vessel 36. The wet crude product/water mixture from static mixer 12 enters separator system 16 about 1" below the top of the water layer via a PFA dip leg 34. A Rosemount 3051 DP transmitter and a Fieldpac PID Controller (not shown) are used in conjunction with control valve 37 to measure and maintain the level of the organic phase in separator system 16.

The organic phase from control valve 37 is collected in a suitable drum such as a FluoroPure PFA composite drum 18. Water that overflows Teflon polymer standpipe 38 is collected in another suitable drum 20 (shown in FIG. 1) such as a high-density polyethylene drum. The vapor space of separator system 16 can be sampled by passage of this stream via line 40 through a caustic bubbler (not shown) and collected using a stainless steel sample bomb (not shown). The wet crude and aqueous waste drums can be located on In scale platform scales having GSE digital weight indicators that display in tenths of pounds.

Operation of a hydrobromination reaction system such as described above, typically involves continuously concurrently feeding propylene (or other olefin having a terminal double bond), molecular oxygen-containing gas, preferably air, and gaseous hydrogen bromide into a reaction zone such as reactor 10 which initially contains on startup, aliphatic bromide to be produced by hydrobromination n-propyl bromide substantially saturated with hydrogen bromide. A preferred operation utilizes propylene as the feed olefin and the reaction zone initially contains on startup, n-propyl bromide substantially saturated with hydrogen bromide. In either case reaction conditions and feed proportions are selected as described previously herein.

Product purification can be carried out using distillation procedures which form no part of this invention.

It is to be understood that chemicals referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Also, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Each and every patent or other publication or published document referred to in any portion of this specification is incorporated in toto into this disclosure by reference, as if fully set forth herein.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

This invention is susceptible to considerable variation in its practice. Therefore the foregoing description is not intended to limit, and should not be construed as limiting, the invention to the particular exemplifications presented hereinabove.

The invention claimed is:

1. A process for the production of propyl bromide, which process comprises continuously feeding propylene, gaseous hydrogen bromide, and a molecular oxygen-containing gas into a liquid phase reaction medium comprised of aliphatic bromide to cause formation of propyl bromide, the feeds being proportioned and maintained to provide a molar excess of hydrogen bromide relative to propylene in the range of about 1 to about 5 percent, and a molar ratio of molecular oxygen to propylene of in the range of about 0.00005:1 to about 0.001:1.

2. A process as in claim 1 wherein the aliphatic bromide of the liquid phase reaction medium consists essentially of propyl bromide.

3. A process as in claim 1 wherein said molar ratio of molecular oxygen to propyl bromide is in the range of about 0.00005:1 to about 0.0001:1.

4. A process as in claim 1 wherein the liquid phase reaction medium is maintained in a temperature range of about −20° C. to about 50° C.

5. A process as in claim 1 wherein the molecular oxygen-containing gas being fed is air.

6. A process as in claim 1 wherein the gaseous hydrogen bromide and molecular oxygen-containing gas are premixed and fed as a combined unitary feed into said liquid phase reaction medium.

7. A process as in claim 1 wherein:
   a) the aliphatic bromide of the liquid phase reaction medium consists essentially of propyl bromide;
   b) the liquid phase reaction medium is maintained in a temperature range of about −20° C. to about 50° C.;
   c) the molecular oxygen-containing gas being fed is air; and
   d) the molar ratio of molecular oxygen to propylene is in the range of about 0.00005:1 to about 0.001:1.

8. A process as in claim 1 wherein the liquid phase reaction medium consists essentially of propyl bromide corresponding to the propyl bromide being produced in the process.

9. A process as in claim 1 wherein the liquid phase reaction medium consists essentially of n-propyl bromide in an amount of about 97.5 wt % or more and isopropyl bromide in an amount of about 2.5 wt % or less.

10. A process as in claim 1 wherein the liquid phase reaction medium consists essentially of n-propyl bromide in an amount of about 95 wt % or more and isopropyl bromide in an amount of about 5 wt % or less.

11. A process as in claim 10 wherein the liquid phase reaction medium is maintained in a temperature range of about −20° C. to about 5° C.

12. A process as in claim 10 wherein the molecular oxygen-containing gas being fed is air.

13. A process as in claim 1 wherein the gaseous hydrogen bromide in the feed is (i) free of gaseous hydrogen chloride or (ii) contains an amount of hydrogen chloride that does not result in formation of more than a total of about 35 ppm (wt/wt) of isopropyl chloride in the hydrobromination reaction product.

14. A process as in claim 13 wherein the liquid phase reaction medium consists essentially of n-propyl bromide in an amount of about 95 wt % or more and isopropyl bromide in an amount of about 5 wt % or less.

15. A process as in claim 13 wherein the molecular oxygen-containing gas being fed is air.

16. A process as in claim 1 wherein:
   a) the gaseous hydrogen bromide in the feed contains hydrogen chloride in an amount that would result in formation of more than a total of about 35 ppm (wt/wt) of isopropyl chloride in the hydrobromination reaction product, said amount of hydrogen chloride being no more than about 5 mole percent % based on the total moles of hydrogen bromide and hydrogen chloride present in the feed;
   b) the liquid phase reaction medium is maintained in a temperature range of about −40° C. to about 5° C.; and
   c) the hydrobromination reaction is performed in a reaction zone from which there is no separate vent of gas.

17. A process as in claim 16 wherein the liquid phase reaction medium is maintained in a temperature range of about −20° C. to about 5° C.

18. A process as in claim 16 wherein the liquid phase reaction medium consists essentially of n-propyl bromide in an amount of about 95 wt % or more and isopropyl bromide in an amount of about 5 wt % or less.

19. A process as in claim 16 wherein the molecular oxygen-containing gas being fed is air.

20. A process as in claim 16 wherein the molar ratio of molecular oxygen to olefin is in the range of about 0.00005:1 to about 0.0001:1; wherein the liquid phase reaction medium is maintained in the range of about 0° C. to about 5° C.; and wherein the liquid phase reaction medium consists essentially of n-propyl bromide in an amount of about 95 wt % or more and isopropyl bromide in an amount of about 5 wt % or less.

21. A process for the production of an aliphatic bromide in which the bromine atom is attached to a terminal carbon atom, which process comprises continuously feeding propylene, gaseous hydrogen bromide, and a molecular oxygen-containing gas into a reaction zone which initially contains n-propyl bromide substantially saturated with hydrogen bromide, the feeds being proportioned and maintained such that they supply into the reaction zone a molar excess of hydrogen bromide relative to propylene in the range of about 1 to about 5 percent, and a molar ratio of molecular oxygen to olefin in the range of about 0.00005:1 to about 0.001:1.

22. A process as in claim 21 wherein the gaseous hydrogen bromide is devoid or essentially devoid of HCl and wherein upon reaching steady-state conditions, the reaction zone is maintained at elevated pressure of about 5-25 psig minimum, and in a temperature range of about 20 to about 50° C.

23. A process as in claim 21 wherein the gaseous hydrogen bromide contains HCl in an amount in the range of about 0.1 to about 5 mole % and wherein upon reaching steady-state conditions, the reaction zone is maintained at elevated pressure of about 5-25 psig minimum, and in a temperature range of about −40 to about 5° C.

* * * * *